United States Patent [19]

Freed

[11] 4,414,389
[45] Nov. 8, 1983

[54] 4-SUBSTITUTED-PIPERIDINO CARBOXAMIDES

[75] Inventor: Meier E. Freed, Paoli, Pa.

[73] Assignee: American Home Products Corporation, New York, N.Y.

[21] Appl. No.: 381,673

[22] Filed: May 25, 1982

[51] Int. Cl.³ .................. C07D 487/04; A61K 31/495
[52] U.S. Cl. ..................................... 544/349; 424/250
[58] Field of Search ........................................ 544/349

[56] References Cited

U.S. PATENT DOCUMENTS

| | | | |
|---|---|---|---|
| 3,388,128 | 6/1968 | Day et al. | 544/349 |
| 4,188,389 | 2/1980 | Jirkovsky | 544/349 |
| 4,230,856 | 10/1980 | Skoldinov et al. | 544/349 |
| 4,339,579 | 7/1982 | Freed | 544/349 |

OTHER PUBLICATIONS

Derwent Abstract 79789T-B.
Derwent Abstract 17446V/10.

Freed et al., J. Org. Chem. 25 2108–2113 (1960).

*Primary Examiner*—Mark L. Berch
*Assistant Examiner*—C. Kalita
*Attorney, Agent, or Firm*—Richard K. Jackson

[57] ABSTRACT

The compounds

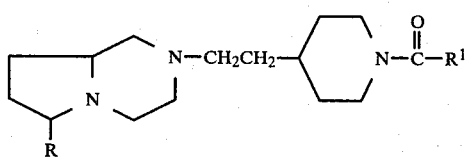

where R is hydrogen, alkyl, phenyl or substituted phenyl and $R^1$ is 2-furanyl, 2-benzofuranyl, 2-thienyl or 2-pyridyl or pharmaceutically acceptable salts thereof are antihypertensive, antisecretory agents.

6 Claims, No Drawings

4-SUBSTITUTED-PIPERIDINO CARBOXAMIDES

DESCRIPTION OF THE INVENTION

In accordance with this invention there is provided a group of compounds of the formula:

The compounds of this invention are produced by addition of 4-vinylpyridine to hexahydro-6-phenylpyrrolo[1,2-a]pyrazine or 1,4-diazabicyclo[4.3.0]nonane followed by hydrogenation to saturate the pyridine ring and acylation with the desired 2-furanoyl halide, 2-benzofuranyl halide, 2-thienoyl halide or 2-pyridoyl halide, thusly:

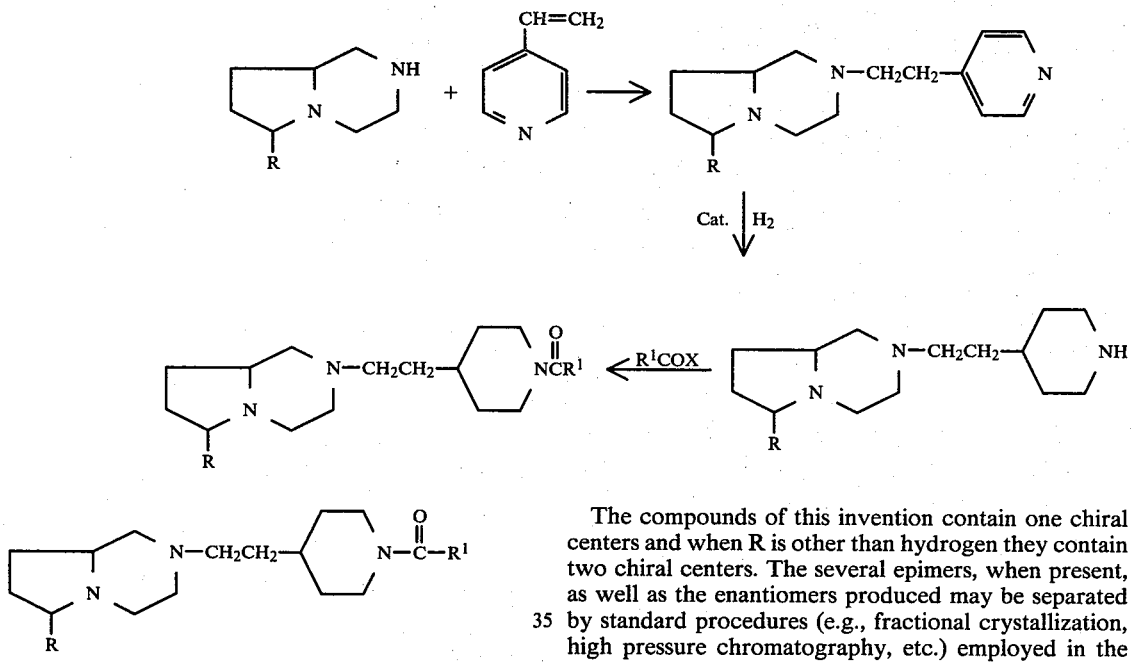

in which
R is hydrogen, alkyl of 1 to 6 carbon atoms, phenyl or substituted phenyl in which the substituent is alkyl of 1 to 6 carbon atoms, alkoxy of 1 to 6 carbon atoms, fluoro or chloro and said substituent is in the ortho or para position;
$R^1$ is 2-furanyl, 2-benzofuranyl, 2-thienyl or 2-pyridyl;

or a pharmaceutically acceptable salt thereof, which compounds act an anti-hypertensive agents and gastric anti-secretory agents by virtue of which they are useful in the treatment of mammals suffering from hypertension and peptic ulcer disease which dysfunctions frequently occur simultaneously in the same patient.

As anti-hypertensive agents, the compounds of this invention lower blood pressure in patients suffering from elevated blood pressure.

As anti-secretory agents, the compounds of this invention reduce (1) total gastric volume, (2) hydrogen ion secretion, or (3) hydrogen ion concentration. The reduction of any one of these parameters aids in attenuating the general debilitating influence of a peptic ulcer in humans. The use of compounds exhibiting anti-secretory activity in the curative and/or prophylactic treatment of peptic ulcer disease is an established, beneficial procedure.

The pharmaceutically acceptable salts of the compounds of this invention are produced from inorganic or organic acids such as hydrochloric, hydrobromic, sulfuric, phosphoric, nitric, formic, acetic, propionic, oxalic, succinic, glycollic, lactic, malic, tartaric, citric, ascorbic, maleic, phenylacetic, benzoic, para-amino-benzoic, salicylic, methanesulfonic acid, and the like.

The compounds of this invention contain one chiral centers and when R is other than hydrogen they contain two chiral centers. The several epimers, when present, as well as the enantiomers produced may be separated by standard procedures (e.g., fractional crystallization, high pressure chromatography, etc.) employed in the resolution of such mixtures.

Each of the anti-secretory agents of this invention is active in the following scientifically recognized, standard test for gastric anti-secretory activity:

Male Charles River rats of Spraque-Dawley strain and 190 to 240 grams body weight are food deprived for 24 hours with water ad libitum until the test. Groups of ten rats each are assigned to either control or drug treatment. Pyloric ligation was performed under ether anesthesia through a midline laparotomy, and either control vehcle (0.25 methylcellulose) or drug in control vehicle was administered intraduodenally (i.d.) The rats are sacrificed by $CO_2$ asphyxiation four hours after pyloric ligation. The stomachs are removed and the gastric contents emptied into graduated centrifuge tubes. The gastric samples are centrifuged for 20 minutes and those obviously contaminated by food, blood or feces are discarded. The volume of gastric fluid is recorded and the acid concentration of 1.0 milliliter sample aliquots is measured by electrometric titration to pH 7.0 with 0.1 N NaOH. The calculated product of gastric volume (ml/4 hr) and acid concentration (mEq/L) estimates the total acid output (TAO, mEq/4 hr) over the four-hour test period. An analysis of variance is performed on these data to determine statistically significant ($p<0.05$) deviation between control versus drug-treated groups.

The blood pressure lowering ability of the compounds of this invention was established by measuring the systolic pressure of male spontaneously hypertensive rats with a Decker Caudal Plethysmograph. The compounds tested were administered orally and blood pressure was read prior to and at 1.5 and 4 hours after drug administration.

The results of those tests are presented at the conclusion of the following preparatory examples.

The compounds of this invention may be administered orally or parenterally to a mammal in conventional dosage forms at a dose of from about 25 to 100 milligrams per kilogram in single or plural doses depending upon the severity of the hypertensive state and/or the peptic ulcer disease.

Oral administration in solid form by tablet or capsule may be accomplished with the compounds of this invention in neat or pure form alone or in combination with conventional adjuvants. Similarly, parenteral administration may be accomplished with physiological saline or via suspension in conventional vehicles. In any event, the dosing regimen must be individualized by the attending physician for the patient based upon the severity of the dysfunction.

The following examples are presented for purposes of illustration rather than limitation on the scope of the invention. The compounds prepared are representative of the other compounds of the invention.

EXAMPLE 1

1-(2-Furanylcarbonyl)-4-[2-(hexahydro-6-phenylpyrrolo[1,2-a]pyrazine-2(1H)yl)ethyl]piperazine A solution of hexahydro-6-phenylpyrrolo[1,2-a]pyrazine (4.4 g, 0.022 mole), 4-vinylpyridine (5.04 g, 0.044 mole), acetic acid (2.64 g, 0.044 mole) in 40 ml methanol was refluxed 18 hours. After cooling, the solvent was removed under reduced pressure. The residue was redissolved in water (150 ml), treated with potassium carbonate to pH 10-10.5. The oil was extracted into diethyl ether, washed with saline, and dried over sodium sulfate. After filtering off the drying agent the ether was stripped off and the residula oil was distilled, giving 4.3 g. of 2-(4-pyridinyl ethyl)-hexahydro-6-phenylpyrrolo[1,2-a]pyrazine, dihydrochloride, distilling at 178°-85° C./0.05 mm. A one gram aliquot was converted to the dihydrochloric acid salt in acetone. 0.73 g. was obtained; m.p. 157°-8° C.

Calculated: C, 69.83; H, 7.62; N, 12.22; Cl, 10.33. Found: C, 69.47; H, 7.33; N, 12.16; Cl, 10.35.

A solution of 10.1 g. of 2-(4-pyridylethyl)-hexahydro-6-phenylpyrrolo[1,2-a]pyrazine (0.033 mole), dissolved in a mixture of 60 ml ethanol, 12 ml of concentrated hydrochloric acid, and one gram of platinum dioxide was shaken under hydrogen at 45 psi. After a theoretical amount of hydrogen was taken up, the reaction was halted. The catalyst was washed with water. The filtrate was then concentrated to a small volume, made strongly basic and the product extracted into diethyl ether. The organic layer was washed (saline) and dried over MgSO4. After filtering off the drying agent and concentrating the filtrate the residual oil was distilled (b.p. 175°-88° C./0.2 mm). 6.8 g. (67% yield) of 4-(2-(hexahydro-6-phenylpyrrolo[1,2-a]pyrazine-2(1H)-yl)ethylpiperidine, hydrochloride was obtained.

To a solution of 4[2(hexahydro-6-phenylpyrrolo[1,2-a]pyrazin-2(1H)-yl)ethyl]piperidine (1.5 g, 0.005 mole) in 15 ml of dry pyridine, cooled to 5° C., was added a solution of 2-furanoyl chloride (0.78 g, 0.005 mole) in 10 ml of dry benzene. After the addition was completed the reaction was stirred overnight at room temperature. Solvents were then removed under vacuum. The residue was redissolved in a small quantity of water, made basic with potassium carbonate, and extracted into diethyl ether. The ether layer was washed with water and dried over anhydrous sodium sulfate. After filtering, the solution was concentrated under reduced pressure leaving an oily substance. This was redissolved in 50 ml anhydrous diethyl ether and treated with an ethereal solution of fumeric acid. An oily product separated. Decanted of ether. On standing, crystallization occurred. The crystals were filtered off, washed repeatedly with diethyl ether, and dried. 0.3 g of the title compound product was obtained; m.p. 201°-202° C.

Analysis for: $C_{29}H_{37}N_3O_6 \cdot \frac{1}{2}H_2O$: Calculated C, 65.38; H, 7.19; N, 7.89. Found: C, 65.21; H, 7.40; N, 7.74.

Blood pressure:
  50 mg/kg; −22 at 1.5 hours; −49 at 4 hours.
  25 mg/kg; −22 at 1.5 hours; −24 at 4 hours.

Anti-secretory: 89% inhibition of total acid secretion at 32 mg/kg.

EXAMPLE 2

1-(2-Furanylcarbonyl)-4-[2-(hexahydropyrrolo[1,2-a]pyrazin-2(1H)-yl)-ethyl]piperidine A solution of 12 g (0.095 mole) 1,4-diazabicyclo[4.3.0]-nonane, 10 ml of acetic acid and 12.5 ml of 4-vinylpyridine in 225 ml methanol was heated at reflux for 20 hours. The solvent was removed under vacuum and the residue distilled to yield 5.1 g of 2(4-pyridylethyl)pyrrolo[1,2-a]pyrazine; b.p. 126°-130/0.01 mm.

A pressure bottle was charged with 1 g PtO2, 4.5 g of 2-(4-pyridylethyl)pyrrolo[1,2-a]pyrazine (0.0195 mole), 180 ml aqueous ethanol (2/1), and 13 ml of concentrated hydrochloric acid and shaken under 60 psi on a Parr hydrogenation apparatus. When hydrogenation was completed the reaction mixture was filtered free of catalyst, the catalyst washed with ethanol and the combined filtrate concentrated under reduced pressure. The residue was crystallized from methanol. There was obtained 5.5 g (80%) of 2-(4-piperidylethyl)-pyrrolo[1,2-a]pyrazine as the hydrochloride; m.p. 295°-298° C.

Analysis for: $C_{14}H_{27}N_3 \cdot 3HCl \cdot \frac{1}{2}H_2O$: Calculated: C, 47.25; H, 8.76; N, 11.81; Cl, 29.90. Found: C, 47.26; H, 8.26; N, 11.95; Cl, 30.13.

2-(4-Piperidylethyl)-pyrrolo[1,2-a]pyrazine (6 g) was converted to free base with aqueous sodium hydroxide. The organic base was extracted into diethyl ether, washed with saline, and dried. After filtering off the drying agent the solution was concentrated to an oil. This was dissolved in 50 ml of piperidine, cooled by 5° C., and treated with 3.5 ml of toluene. Stirred at 25° C. for 6 hours. The suspension was diluted with methylenedichloride and filtered. The filtrate was concentrated under reduced pressure. The residue was crystallized from acetone. The base, dissolved in acetone was treated with methanolic hydrogen chloride. This hydrochloride was recrystallized from 2-propanol, giving a dihydrochloride of the title compound; m.p. 247°-251° C.

Analysis for: $C_{18}H_{29}N_3O_2 \cdot 2HCl$: Calculated: C, 56.43; H, 10.39; N, 10.39; Cl, 17.53. Found: C, 55.94; H, 10.07; N, 10.07; Cl, 17.15.

Blood Pressure:
  50 mg/kg; −15 at 1.5 hours; −46 at 4 hours.
  25 mg/kg; −31 at 1.5 hours; −52 at 4 hours.

Anti-secretory: 73% inhibition of total acid secretion at 32 mg/kg; and 61% at 16 mg/kg.

EXAMPLE 3

1-(2-Pyridylcarbonyl)-4-[2-(hexahydropyrrolo[1,2-a]pyrazin-2(1H)-yl)ethyl]piperidine In the manner of Example 2, 2-(4-piperidylethyl)pyrrolo[1,2-a]pyrazine and 2-pyridine carbonyl chloride will react in pyridine solution to give the title compound.

EXAMPLE 4

1-(2-Thienylcarbonyl)-4-[2-(hexahydropyrrolo[1,2-a]pyrazine-2(1H)-yl)ethyl]piperidine In the manner of Example 2, 2-(4-piperidylethyl)-pyrrolo[1,2-a]pyrazine and 2-thienylcarbonyl chloride will react in pyridine solution to produce the title compound.

EXAMPLE 5

1(2-Benzofuranylcarbonyl)-4-[2-(hexahydropyrrolo[1,2-a]pyrazine-2(1H)-yl)ethyl]piperidine In the manner of Example 2, 2-(4-piperidylethyl)pyrrolo[1,2-3]pyrazine and 2-benzofuranylcarbonyl chloride will react in solution to give the title compound.

What is claimed is:

1. A compound of the formula

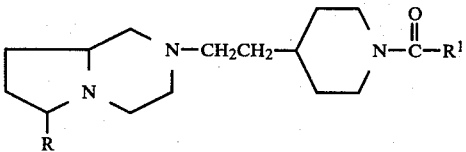

in which
R is hydrogen, alkyl of 1 to 6 carbon atoms, phenyl or mono-substituted phenyl in which the substituent is alkyl of 1 to 6 carbon atoms, alkoxy of 1 to 6 carbon atoms, fluoro or chloro and said substituent is in the ortho or para position;
$R^1$ is 2-furanyl, 2-benzofuranyl, 2-thienyl or 2-pyridyl;
or a pharmaceutically acceptable salt thereof.

2. The compound of claim 1 which is 1-(2-furanylcarbonyl)-4-[2-(hexahydro-6-phenylpyrrolo[1,2-a]pyrazine-2(1H)-yl)ethyl]piperidine or a pharmaceutically acceptable salt thereof.

3. The compound of claim 1 which is 1-(2-furanylcarbonyl)-4-[2-(hexahydropyrrolo[1,2-a]pyrazin-2(1H)-yl)ethyl]piperidine or a pharmaceutically acceptable salt thereof.

4. The compound of claim 1 which is 1-(2-pyridylcarbonyl)-4-[2-(hexahydropyrrolo[1,2-a]pyrazin-2(1H)-yl)ethyl]piperidine or a pharmaceutically acceptable salt thereof.

5. The compound of claim 1 which is 1-(2-thienylcarbonyl)-4-[2-(hexahydropyrrolo[1,2-a]pyrazine-2(1H)-yl)ethyl]piperidine or a pharmaceutically acceptable salt thereof.

6. The compound of claim 1 which is 1-(2-benzofuranylcarbonyl)-4-[2-hexahydropyrrolo[1,2-a]pyrazin-2(1H)-yl)ethyl]piperidine or a pharmaceutically acceptable salt thereof.

* * * * *